United States Patent [19]

Guarino et al.

[11] Patent Number: 5,077,214
[45] Date of Patent: Dec. 31, 1991

[54] USE OF BACULOVIRUS EARLY PROMOTERS FOR EXPRESSION OF FOREIGN GENES IN STABLY TRANSFORMED INSECT CELLS

[75] Inventors: Linda A. Guarino; Donald L. Jarvis, both of Bryan, Tex.

[73] Assignee: The Texas A&M University System, College Station, Tex.

[21] Appl. No.: 377,017

[22] Filed: Jul. 7, 1989

[51] Int. Cl.$^5$ .................... C12N 5/06; C12N 15/06; C12N 15/15

[52] U.S. Cl. ................ 435/240.2; 435/172.3; 435/320.1; 435/240.1; 435/240.21; 435/172.1; 935/70; 935/60; 935/55

[58] Field of Search .............. 435/320, 240.2, 172.3, 435/948, 91, 252.3, 240.1, 240.21; 935/70

[56] References Cited

U.S. PATENT DOCUMENTS 4,745,051  5/1988  Smith et al. .
4,945,050  7/1990  Sanford et al. .................. 435/172.1

OTHER PUBLICATIONS

Old et al. (eds.) 1985 in: *Principles of Gene Manipulation an Introduction to Genetic Engineering*, Blackwell Scientific Publications, Third Edition, pp. 233-234, 251-252.
Nester et al., 1978 in *Microbiology*, Second Edition, Holt, Rinehart and Winston, New York, p. 700.
Baker, 1982 in *The Study of Biology*, Addison-Wesley Publ. Co., New York, p. 905.
Oppermann, H. 1987 in *Developments in Biological Standardization*, (Spier et al., eds. acting) vol. 66, 31-37.
Cullen, B. R. 1987, Methods Enzymol. 152, 684-704.
Klein et al., 1988 Proc. Natl. Acad. Sci. U.S.A. 85, 8502-8505.
Zelenin et al., 1989 Fgbs Lett. 244, 65-67.
Hay et al. (eds.) 1988 in: *Am. Type Cult. Collection Catalogue of Cell Liner and Hybridanar*, Sixth Edition, ATCC, pp. 166-167.
Asubel et al., 1989 *Cunr. Protocols. in Molec. Biol.*, pp. 9.1.4, 9.4.1-9.5.2.
Summers and Smith (1987), A Manual of Methods for Baculovirus Vectors and Insect Cell Culture Procedures, Texas Agricultural Experiment Station Bulletin No. 1555.
Luckow and Summers (1988), "Trends in the Development of Baculovirus Expression Vectors," Bio/Technology 6:47-55.

(List continued on next page.)

*Primary Examiner*—Jacqueline Stone
*Assistant Examiner*—Christopher S. F. Low
*Attorney, Agent, or Firm*—Arnold, White & Durkee

[57] ABSTRACT

The present invention provides an alternative strategy for baculovirus-mediated foreign gene expression: the promoters from immediate-early or delayed-early baculovirus viral genes were used to obtain the continuous expression of foreign genes in stably-transformed insect cells. The IE1 or the 30K promoters from *Autographa californica* nuclear polyhedrosis virus can drive the continuous expression of a foreign gene in insect cells. IE1-$\beta$-galactosidase or 39K-$\beta$-galactosidase constructs were used in combination with the IE1-neomycin resistance construct to cotransfect *Spodoptera frugiperda* (Sf9) cells. Neomycin-resistant clones were selected and analyzed for $\beta$-galactosidase expression. A high percentage of the transformants expressed $\beta$-galactosidase activity and contained polypeptides which appeared to be authentic $\beta$-galactosidase. Analysis of high molecular weight DNA from the IE1Neo/IE1-$\beta$gal cotransformants showed that plasmid sequences were integrated and maintained for 20-55 passages in culture. Further analysis of the clones expressing $\beta$-galactosidase from the IE1 promoter showed that they contained integrated plasmid DNA sequences and that the $\beta$-galactosidase-encoding transcripts initiated specifically within the IE1 promoter. Thus, early baculovirus promoters may be used for foreign gene expression in stably-transformed insect cells with the advantages of continuous expression and minimal degradation of recombinant protein products.

6 Claims, 1 Drawing Sheet

OTHER PUBLICATIONS

Doerfler (1986), "Expression of the Autographa californica Nuclear Polyhedrosis Virus Genome in Insect Cells: Homologous Viral and Heterologous Vertebrate Genes the baculovirus Vector System," *Cur. Topics Microbiol. Immunol.* 131:51–68.

Friesen and Miller (1986), "The Regulation of Baculovirus Gene Expression," Cur. Topics Microbiol. Immunol. 131:31–49.

Jarvis and Summers (1989), "Glycosylation and Secretion of Human Tissue Plasminogen Activator in Recombinant Baculovirus-Infected Insect Cells," Mol. Cell. Biol. 9:214–223.

Carson et al. (1988), "Functional Mapping of an AcNPV Immediately Early Gene which Augments Expression of the EI-1 Trans-Activated 39K Gene," Virol. 162:444–451.

Luckow and Summers (1988), "Signals Important for High-Level Expression of Foreign Genes in Autographa californica Nuclear Polyhedrosis VIrus Expression Vectors," Virol. 167:56–71.

Guarino and Summers (1987), "Nucleotide Sequence and Temporal Expression of a Baculovirus Regulatory Gene," J. Virol. 61:2091–2099.

Guarino and Summers (1986), "Functional Mapping of a Trans-Activating Gene Required for Expression of a Baculovirus Delayed-Early Gene," J. Virol. 57:563–571.

Guarino and Summers (1986), "Interspersed Homologous DNA of Autographa californica Nuclear Polyhedrosis Virus Enhances Delayed-Early Gene Expression," J. Virol. 60:215–223.

Guarino and Summers (1986), "Complete Sequence and Enhancer Function of the Homologous DNA Regions of Autographa californica Nuclear Polyhedrosis Virus," J. Virol. 60:224–229.

1. pIE1Neo 2. p39E⁻Neo 3. p39E⁺Neo 4. pIE139Neo 5. p510Neo 6. pIE1NFB 7. pIE1NFB 8. p39E⁺FB 9. pIE1tPA

USE OF BACULOVIRUS EARLY PROMOTERS FOR EXPRESSION OF FOREIGN GENES IN STABLY TRANSFORMED INSECT CELLS

The Government may have rights in this invention pursuant to a funding agreement with the National Science Foundation (NSF), Grant No. DMB-88 04732.

BACKGROUND OF THE INVENTION

A. Field of the Invention

This invention relates to the production of stably-transformed insect cell lines capable of continuous expression of a selected foreign gene product.

B. Description of the Related Art

Baculovirus expression vectors (BEVs) have become extremely important tools for the expression of foreign genes, both for basic research and for the production of proteins with direct clinical applications in human and veterinary medicine (W. Doerfler, *Curr. Too. Microbiol. Immunol.*, 131:51–68 (1968); V. A. Luckow and M. D. Summers, *Bio/Technology*. 6:47–55 (1988a); L. K. Miller, *Annual Review of Microbiol.*, 42:177–199 (1988); M. D. Summers, *Curr. Communications in Molecular Biology*. Cold Spring Harbor Press, Cold Spring Harbor, N.Y. (1988)). BEVs are recombinant insect viruses in which the coding sequence for a chosen foreign gene has been inserted behind the promoter in place of the nonessential viral gene, polyhedrin (Smith and Summers, U.S. Pat. No. 4,745,051).

Baculovirus genes are expressed in a sequential, temporally-regulated fashion during one or more of four different phases of the viral replication cycle (P. D. Friesen and L. K. Miller, *Curr. Too. Microbiol. Immunol.*, 131:31–49 (1986); L. A. Guarino, *CRC Press*, (1989) [in press]). Therefore, different baculovirus genes may be classified as immediate-early ($\alpha$), delayed-early ($\beta$), late ($\gamma$), or very late ($\delta$), according to the phase of the viral infection during which they are expressed. The expression of these genes occurs sequentially, probably as the result of a "cascade" mechanism of transcriptional regulation. Thus, the immediate-early genes are expressed immediately after infection, in the absence of other viral functions, and one or more of the resulting gene products induces transcription of the delayed-early genes. Some delayed-early gene products, in turn, induce transcription of late genes, and finally, the very late genes are expressed under the control of previously expressed gene products from one or more of the earlier classes. One relatively well-defined component of this regulatory cascade is IE1, an immediate-early gene of *Autographa californica* nuclear polyhedrosis virus (AcMNPV). IE1 is expressed in the absence of other viral functions and encodes a product that stimulates the transcription of several genes of the delayed-early class, including the 39K gene (L. A. Guarino and M. D. Summers, *J. Virol.*, 57:563–571 (1986a); *J. Virol.*, 61:2091–2099 (1987)), as well as late genes (L. A. Guarino and M. D. Summers, *Virol.*, 162:444–451 (1988)). However it is believed that the immediate-early genes are not dependent upon other viral gene for expression.

The polyhedrin gene is classified as a very late gene. Therefore, transcription from the polyhedrin promoter requires the previous expression of an unknown, but probably large number of other viral and cellular gene products. Because of this, state-of-the-art BEVs, such as the exemplary BEV system described by Smith and Summers (U.S. Pat. No., 4,745,051) will express foreign genes only as a result of gene expression from the rest of the viral genome, and only after the viral infection is well underway. This represents a clear limitation to the use of existing BEVs for at least two reasons. First, infection with the essentially intact recombinant virus ultimately kills the host cell, thereby terminating its role as a "factory" for foreign protein production. Thus, prior art BEV systems are limited to gene expression in transient cell lines. Second, the ability of the host cell to process newly synthesized proteins decreases as the baculovirus infection progresses (D. L. Jarvis and M. D. Summers, *Mol. Cell. Biol.*, 9:214–223 (1989)). Thus, gene expression from the polyhedrin promoter occurs at a time when the host cell's ability to process newly synthesized proteins is significantly diminished. As a consequence, the expression of secretory glycoproteins in BEV systems is complicated due to incomplete secretion of the cloned gene product, thereby trapping the cloned gene product within the cell in an incompletely processed form.

SUMMARY OF THE INVENTION

This invention provides a stably-transformed insect cell line capable of continuous expression of a selected gene product, comprising a host insect cell, such as a Lepidopteran cell, having integrated into its genome a heterologous DNA sequence comprising an early baculovirus promoter, an ATG start signal and heterologous DNA of the desired protein in the proper orientation to allow transcription of the cloned gene. Such cell lines are capable of constitutive expression of heterologous genes from such diverse exogenous sources as prokaryotes (i.e., $\beta$-galactosidase), and eukaryotes (i.e., tissue plasminogen activator) as well as from other viral genes (i.e., hepatitis B antigen).

The present invention overcomes many of the limitations of the prior art by employing a strategy for baculovirus-mediated foreign gene expression in the absence of the cytotoxic effects of the virus by involving the use of baculovirus early promoters, such as the AcMNPV IE1 (immediate-early) or AcMNPV 39K (delayed-early) genes. Where the input plasmid DNA is integrated into the host cell genome, such host cell is stably-transformed. The stably-transformed insect cells contain integrated copies of the baculovirus early promoter, an ATG start signal, and heterologous DNA of a desired protein in proper orientation to allow transcription of the cloned gene. The stably-transformed cells of the present invention can produce the desired protein continuously for more than 55 passages in culture. Baculovirus immediate-early or delayed-early promoters can be used for the expression of foreign genes in stably-transformed insect cells, with the advantages of continuous expression, minimal degradation, and optimal processing of the recombinant protein product.

In a preferred embodiment, a stably-transformed insect cell line capable of continuously expressing a heterologous gene is provided by the present invention via a method which entails constructing two plasmids. One plasmid construction contains a selectable gene immediately down stream of a promoter region of one of a baculovirus early gene. The other plasmid contains the heterologous gene of interest downstream of a promoter region of the same or a similar baculovirus early gene. A mixture of these two plasmid constructions is then used to cotransfect the insect cells (the selectable gene serving as a marker and positive control for incorporation of one or both plasmids into the cell). Subsequent to the cotransfection step, the cells are cultured under conditions which select against those cells which have not incorporated the selective marker gene-containing plasmid.

After extended growth of the colonies selected for the presence of the marker gene, each colony is assayed for the presence of the heterologous gene. Additional periods of growth are allowed for those colonies which are both capable of growth under the specific selective conditions and which are determined to contain the heterologous gene. Those colonies which continue to exhibit these two traits are said to be stably-transformed.

The method of the invention can be applied to Lepidopteran insect cells including those derived from *Spodoptera frugiperda* and *Trichoplusia ni*. In a preferred embodiment of the invention, the cell line which is cotransfected is the Sf9 cell line of *Spodopotera frugiperda*. In its most preferred embodiment, the Sf9 cells utilized will be those cells which are in the log phase of growth.

The method allows the stable transformation of a cell line with heterologous genes from a variety of sources. In one embodiment, a eukaryotic gene encoding human tissue plasminogen activator is stably incorporated into the cell line. In another embodiment, a prokaryotic gene from bacteria encoding β-galactosidase is stably incorporated into the cell line.

The method of the invention relies on the surprising finding that early gene promoter regions of an otherwise lethal infecting virus can be used individually and separately from the infecting virus genome to stably transform insect cell lines. Equally surprising is the fact that expression of heterologous genes under the control of these early gene promoter regions is both constitutive and, yet, is not deleterious to the cell, thereby allowing fidelitous processing of post-translationally modified cloned foreign gene products.

In one embodiment, the early gene promoter region is derived from a baculovirus. The baculovirus can be any one of a number of viruses of insect cells including *Autographa californica* MNPV, *Trichoplusia ni* MNPV, *Rachiplusia ou* MNPV and *Galleria mellonella* MNPV. In a most preferred embodiment, the early gene promoter region is isolated from the baculovirus *Autographa californica* MNPV, where said early gene promoter region is capable of being expressed in the cells of *Spodopotera frugiperda*. The early gene promoter region isolated from baculovirus may be an immediate-early gene of the virus such that no additional viral gene or gene product is needed in order to get constitutive expression of the heterologous gene. The immediate-early gene from which the promoter region is derived may be either IEl or IEN. In a preferred embodiment, the gene promoter region is isolated from the immediate-early gene of baculovirus, IEl.

In another embodiment of the invention, an immediate-early gene as described above is used in combination with a baculovirus gene promoter region of the delayed-early category. Unlike the immediate-early genes, such delayed-early genes require the presence of other viral genes or gene products such as those of the immediate-early genes. The combination of immediate-early genes can be made with any of several delayed-early gene promoter regions such as 39K or one of the delayed-early gene promoters found on the HindIII-k fragment of the baculovirus genome. In a preferred embodiment, the 39K promoter region is linked to the heterologous gene of interest and expression is further controlled by the presence of IEl.

Additionally, when a combination of immediate-early genes with a delayed-early gene promoter region is used, enhancement of the expression of heterologous genes can be realized by the presence of an enhancer sequence in direct cis linkage with the delayed-early gene promoter region. Such enhancer sequences are characterized by their enhancement of delayed-early gene expression in situations where the immediate-early gene or its product is limited. In a preferred embodiment, the hr5 enhancer sequence is linked directly (in cis) to the delayed-early gene promoter region, 39K, thereby enhancing the expression of the cloned heterologous DNA.

Once the cotransfection has integrated both the selectable gene and the heterologous DNA coding for a desired protein into the insect cell line, it is necessary to analyze the resulting colonies of transformed cells for the presence of the heterologous DNA. The presence of this DNA may be detected directly by any of a number of analytical techniques which are known to those skilled in the art of gene cloning, including, a direct probe of the transformed cell line's DNA for homologous sequences corresponding to that of the cloned DNA. Indirectly, the presence of the DNA may be determined by techniques known to those skilled in the art of gene cloning which allow detection of specifically promoted transcripts (RNA). In another embodiment, immunoassays utilizing radiolabelled or enzyme-linked antibody probes may be used to detect the presence of the heterologous DNA product (protein).

Once the method of the invention is utilized as described above, it is possible to derive the stably-transformed cell line of interest. In the most preferred embodiment, a stably-transformed Sf9 cell line of *Spodoptera frugiperda* is constructed which expresses a heterologous DNA of interest under the control of any early gene promoter or combination of early gene promoters for over 55 passages of growth. The heterologous DNA product of such a stably-transformed cell line is, in the most preferred embodiment, post-translationally modified and/or secreted by the cell line since the cellular machinery of these cells is substantially unchanged by the presence of the early gene sequences of the virus.

One of the most important potential improvements represented by this invention, compared to the use of the polyhedrin promoter in a transient BEV system, is that the stably-transformed cells are healthy during the entire time the foreign gene is expressed. This means that protein processing, which might be hindered in the BEV setting could proceed smoothly. Thus, for the expression of secretory and membrane-bound-glycoproteins, for which the BEV system has generally been less successful, the new approach of this invention is much more efficient.

Another potential advantage of the stably-transformed cell approach is that the product might be easier to purify. Immunoprecipitation and western analyses suggested that the recombinant baculovirus-infected Sf9 cells from the transient BEV system contained significant amounts of β-gal degradation products, even after only 24 hours of infection. This is, most likely, an unavoidable by-product of the cytopathic effect of the virus which induces the intracellular release of proteolytic enzymes that can degrade the recombinant protein product. Whether or not this speculation is correct, the presence of the degradation products would complicate purification of the β-gal product from the transient BEV-infected cells. This problem can be avoided by isolating the product from stably-transformed Sf9 cells as described herein.

DETAILED DESCRIPTION OF THE PREFERRED EMBODIMENTS

Figure 1:
FIG. 1 schematically shows the construction of the recombinant plasmids pIElNeo, p39E⁻Neo, p39E⁺Neo, pIE139Neo, p510Neo, pIE1FB, pIE1 NFB, p39FB and pIE1 tPA.
Figure 1:
Figure 1:
Figure 1:
Figure 1:
Figure 1:
Figure 1:
Figure 1:
Figure 1:

As used herein, the term baculovirus early gene includes baculovirus immediate-early genes and baculovirus delayed-early genes. Immediate-early genes are comprised of any viral gene which is expressed in uninfected cells, and includes the genes IE1 and IEN. Delayed-early genes are any viral genes which are activated in trans by an immediate-early gene product, such as IE1 or IEN. The AcMNPV 39K gene is an exemplary delayed-early gene, as are the four delayed-early transcripts of the HindIII-k fragment of AcMNPV. Transcription from delayed-early genes under the control of immediate-early gene products can be enhanced in the presence of a cis-linked enhancer such as hr1, hr2, hr3, hr4 or hr5.

As used herein, the term heterologous gene or heterologous DNA comprises those exogenous sources of DNA which include eukaryotic genes or DNA, prokaryotic genes or DNA and further includes genes or DNA of viral origin.

Deposit of Plasmids

The preferred plasmid, pIE1 containing the immediate-early baculovirus promoter IE1, was deposited with American Type Culture Collection, (Rockville, Maryland) on July 6, 1989 and is assigned accession number 40630. The preferred plasmid, p39E⁺containing the delayed-early promoter 39K and the transcriptional enhancer element hr5, was deposited with American Type Culture Collection (Rockville, Md.) on July 6, 1989, and is assigned accession number 40629. The preferred plasmid, pHindIIIK containing the four delayed-early transcripts of the HindIII-k fragment of AcMNPV, was deposited with American Type Culture Colelction, (Rockville, Maryland) on July 6, 1989 and is assigned accession number 40628.

EXPERIMENTAL

Starting Materials and Methods

According to the preferred embodiment of this invention, the neomycin resistance gene (Neo-R), is utilized and was obtained according to the methods set forth in P. J. Southern and P. Berg, *J. Mol. Appl. Gen.*, 1:327–341 (1982). However, those skilled in the art who have the benefit of this disclosure will recognize that other antibiotic resistance genes may be suitably utilized. In particular, it is expected that at least the hygromycin B resistance gene (Hygro-R) and the methotrexate resistance gene (Metho-R) obtained according to the methods set forth in J. C. Li and E. Kaminskas, PNAS, 81:5694–5698 (1981) and may be utilized to advantage.

Viral DNA

The baculovirus *Autographa californica* nuclear polyhedrosis virus (AcMNPV), used in the examples as the original source of viral DNA was isolated according to procedures described in G. E. Smith and M. D. Summers, *Virology*, 89:517–520 (1978) and G. E. Smith and M. D. Summers, *J. Virol.*, 39:125–137 (1981).

According to the preferred embodiment of this invention, a particular strain of AcMNPV, E2, may be utilized. However, those skilled in the art who have the benefit of this disclosure will recognize that other baculoviruses and other baculovirus strains may also be suitably utilized to obtain viral DNA. In particular, it is expected that at least the closely related and naturally occurring strains *Trichoplusia ni* MNPV, *Rachiplusia ou* MNPV, *Galleria mellonella* MNPV and any plaque-purified strains such as the M3, R9, S1 and S3 strains of AcMNPV isolated and characterized in G. E. Smith and M. D. Summers, *J. Virol.*, 33:311–319 (1980) may be utilized to advantage. Further description of those and other strains are found in G. E. Smith and M. D. Summers, *Virol.*, 89:517–527 (1978).

Enzymes

Restriction enzymes and other enzymes used in these constructions were obtained either from Bethesda Research Laboratories (Bethesda, Md.), Promega (Madison, Wis.), or New England Biolabs, Inc. (Beverly, Mass.).

β-gal DNA

The DNA fragment comprising the 8-galactosidase gene used in the examples was isolated from the plasmid pDP500, obtained from Dr. Max D. Summers, Dept. of Entomology, Texas A&M University, College Station, Tex, 77843. (See V. A. Luckow and M. D. Summers, *Virol.*, 167:56–71 (1988b)). Plasmids containing the DNA fragment comprising the β-galactosidase gene are available from American Type Culture Collection (Rockville, Md.).

tPA DNA

The DNA fragment comprising the human tissue plasminogen activator gene used in the examples was isolatd from the plasmid pVL327, obtained from Dr. Max D. Summers, Dept. of Entomology, Texas A&M University, College Station, Tex. 77843. (See V. A. Luckow and M. D. Summers, *Virol.*, 167:56–71 (1988b)). Plasmids containing the DNA fragment comprising the human tissue plasminogen activator gene are available from American Type Culture Collection (Rockville, Md.).

Insect Cell Lines

The Lepidopteran insect cell line IPLB-Sf21-AE was established more than ten years ago from the fall armyworm, *Spodoptera frugiperda* (J. L. Vaughn, et al., *In Vitro*, 13:213–217 (1977)).

The *Spodoptera frugiperda* Sf9 cell line was obtained from American Type Culture Collection (Rockville, Md.) and is assigned accession number ATCC CRL 1711. See M. D. Summers and G. E. Smith, *A Manual of Methods for Baculovirus Vectors and Insect Cell Culture Procedures*, Texas Agricultural Experiment Station Bulletin No. 1555, Texas A&M University (1987). Those skilled in the art who have the benefit of this disclosure will recognize that other clonal derivatives of the Sf9 cell line can be utilized to advantage.

Cell Medium

The TNMFH medium used in the examples was prepared according to the methods of M. D. Summers and G. E. Smith, *A Manual of Methods for Baculovirus Vectors and Insect Cell Culture Procedures*. Texas Agricultural Experiment Station Bulletin No. 1555, Texas A&M University (1987). (See also W. F. Hink, *Nature (London)*, 226:466–467 (1970)). The fetal calf serum used to supplement the TNMFH medium can be obtained from Hazelton Research Products, Inc. (Lenexa, Kans.).

Antibiotics

The neomycin antibiotic, G418 used in the examples was obtained from GIBCO, (Grand Island, N.Y.). Hygromycin B and methotrexate antibiotics are also commercially available from Sigma Chemical Company, (St. Louis, Mo.).

Methods

All plasmids were constructed and purified using standard recombinant DNA techniques described in T. Maniatis, E. F. Fritsch and J. Sambrook, *Molecular Cloning: A Laboratory Manual*, Cold Spring Harbor Laboratory (1982) under the current regulations described in United States Dept. of HEW, *National Institute of Health (NIH) Guidelines for Recombinant DNA Research*. These references include procedures for the following standard methods: cloning procedures with *E. coli* plasmids, transformation of *E. coli* cells, plasmid DNA purification, phenol extraction of DNA, ethanol precipitation of DNA, agarose gel electrophoresis, purification of DNA fragments from agarose gels, and restriction endonuclease and other DNA-modifying enzyme reactions.

The standard methods of insect cell culture, cotransfection and preparation of certain plasmids, including pAc510 and pAc360-8-gal, used in accordance with the examples, are set forth in M. D. Summers and G. E. Smith, *A Manual of Methods for Baculovirus Vectors and Insect Cell Culture Procedures*, Texas Agricultural Experiment Station Bulletin No. 1555, Texas A&M University (1987). This reference also pertains to the standard methods of cloning genes into AcMNPV transfer vectors, plasmid DNA isolation, transferring genes into the AcMNPV genome, viral DNA purification, radiolabelling recombinant proteins and preparation of insect cell culture media.

The procedures for the cultivation of viruses and cells are described in L. E. Volkman and M. D. Summers, *J. Virol*, 19:820–832 (1975) and L. E. Volkman, M. D. Summers and C. H. Hsieh, *J. Virol*, 19:820–832 (1976). Viral growth kinetics were determined as described by L. E. Volkman, et al., *supra* using *S. frugiperda* and a 1.5% agarose overlay.

Biochemical analyses

Total cellular DNA was extracted from Sf9 cells (passage 26, hereafter "P26") or clonal derivatives (IE1FB1, P21; IE1FB2, P21; IE1FB4, P20; IE1FB5, P20; and IE1FB7, P19) by standard methods described in T. Maniatis, E. F. Fritsch and J. Sambrook, *Molecular Cloning: Laboratory Manual*, Cold Spring Harbor Laboratory (1982). Hirt lysates were prepared from Sf9 cells or clonal derivatives (IE1FB1, P17; IE1FB2, P16 and 49; IE1FB4, P21; and IE1FB7, P15 as described previously in B. Hirt, *J. Mol. Biol.*, 26:365–369 (1967). DNA samples were analyzed for the presence of plasmid sequences by the method of E. M. Southern, *J. Mol. Biol.*, 98:503–517 (1975). The probes used for Southern analyses were labelled with [α-$^{32}$P]dATP (New England Nuclear, Boston, Mass.; 800 Ci/mmol) by the random primer method of A. P. Feinberg and B. Vogelstein, *Analyt. Biochem.*, 132:6–13 (1983). Southern blots were hybridized and washed under high stringency conditions as described previously in J. G. W. Fleming and M. D. Summers, *J. Virol.*, 57:552–562 (1986). Total cellular RNA was extracted by the method of J. M. Chirgwin et al., *Biochemistry*. 18:5294–5299 (1979), and was subjected to S1 nuclease protection analysis according to the methods in R. F. Weaver and C. Weissman, *Nucleic Acids Res.*, 7:1175–1193 (1979). Probes for S1 mapping were gel-purified restriction fragments 5' end-labeled with polynucleotide kinase. Total cellular proteins were detergent-extracted and analyzed either by the radioimmunoprecipitation methods in S. W. Kessler, *J. Immunol.*, 115:1617–1624 (1975) and the sodium dodecyl sulfate polyacrylamide gel electrophoresis (SDS-PAGE) methods in U. K. Laemmli, *Nature*, 227:680–685 (1970), or by the SDS-PAGE and western blotting methods of H. Towbin, T. Staehlin and J. Gordon, *Proc. Natl. Acad. Sci. U.S.A.*, 76:4350–4354 (1979), as described previously in D. L. Jarvis and M. D. Summers, *Mol. Cell. Biol.*, 9:214–223 (1989). Immune complexes were detected in western blots by the alkaline phosphatase method set forth in M. S. Blake, et al., *Anal. Biochem.*, 36:175–179 (1984). Assays for β-galactosidase activity were performed using a modification of the method of I. Zamn and A. Fowler, in: *The Lactose Operon*, p. 27, Cold Spring Harbor Press, Cold Spring Harbor, New York (1970). Units of β-galactosidase activity are expressed in Tables 1 and 2 as the change in absorbance at 420nm per hour per million cells. One unit of activity equals an increase of 1.0 absorbance units after incubation of the extract from $1 \times 10^6$ cells per one hour.

Immunofluoresence

Indirect immunofluorescence was used to visualize antigens in Sf9 cells or their clonal variants. The cells were grown on coverslips for various time periods, rinsed with PHEM buffer (60mM PIPES, 25 mM HEPES, 10 mM EGTA, 2 mM MgCl$_2$, pH 6.9; REF) and fixed in formaledehyde (2% w/v in PHEM; freshly prepared from paraformaldehyde) for 20 minutes at room temperature. The cells were rinsed with PHEM, treated with 0.1% Triton-X-100 in PHEM for another 20 minutes at room temperature, and rinsed with Dulbecco's phosphate-buffered saline (DPBS). The fixed and solubilized cells then were incubated for 30 minutes in a humidified chamber at room temperature with primary antibody (e.g., mouse-anti-β-galactosidase; Promega; Madison, Wis.) diluted in DPBS containing 2% normal goat serum. The cells were rinsed with DPBS, then incubated with secondary antibody (e.g. goat-anti-mouse-IgG-FITC; Organon Teknika Corporation; West Chester, Pa.) under the conditions described above. Finally, the cells were rinsed with DPBS and water, and mounted for fluorescence microscopy and photography using an Olympus Vanox Model AHBT microscope (Olympus Optical Co., LTD.; Tokyo, Japan.)

EXAMPLE I

Construction of Recombinant Plasmids

All constructs used in the examples are shown schematically in FIG. 1. The plasmid pIE1Neo contains the neomycin resistance gene, Neo-R (P. J. Southern and P. Berg, *J. Mol. Appl. Gen.*, 1:327-341 (1982)), immediately downstream of the IE1 promoter (L. A. Guarino and M. D. Summers, *J. Virol.*, 57:563-571 (1986a); *J. Virol.*, 61:2091-2099 (1987). This plasmid was constructed by inserting a repaired BclII-BamHI fragment encoding Neo-R into a HincII site 39 base pairs upstream of the translational start site for IE1.

The plasmid p39E+Neo contains the promoter for 39K (L. A. Guarino and M. D. Summers, *J. Virol.*, 57:563-571 (1986a)), with the AcMNPV transcriptional enhancer element, hr5, (L. A. Guarino and M. D. Summers, *J. Virol.*, 6):215-223 (1986b); L. A. Guarino et al., *J. Virol.*, 60:24-229 (1986)), located upstream, and the Neo-R gene inserted in frame 7 base pairs downstream of the 5' AUG for the 39K gene. This plasmid was derived from p39CATQ-(L. A. Guarino and M. D. Summers, *J. Virol.*, 57:563-471 (1986a)) by digestion with BstBI, followed by repair with the Klenow fragment of DNA polymerase I, deletion of the CAT sequences with BamHI, and insertion of the BqlII (repaired)-BamHI fragment encoding Neo-R at the BstBI and BamHI sites. According to the preferred embodiment of this invention, the AcMNPV transcriptional enhancer element hr5 may be utilized. However, those skilled in the art who have the benefit of this disclosure will recognize that other transcriptional enhancer elements may also be suitably utilized in combination with a baculovirus early gene or gene promoter. In particular, it is expected that at least the AcMNPV transcriptional enhancer elements hr1, hr2, hr3 and hr4 described and characterized in L. A. Guarino, M. A. Gonzalez and M. D. Summers, *J. Virol.*, 60:224-229 (1986) may be utilized to advantage.

The plasmid p39E−Neo was constructed in similar fashion to the plasmid p39E+Neo. However, p39−Neo lacks the hr5 (or other) enhancer, and is constructed by HindIII digestion and religation of p39E+Neo The plasmid pIE139Neo was derived from p39CAT-/IE-1 (L. A. Guarino and M. D. Summers, J. Virol., 57:563-571 (1986a)) by replacing the BamHI CAT fragment with the BqlII-BamHI fragment encoding Neo-R.

The plasmid p510Neo was constructed by inserting the BqlII-BamHI fragment encoding Neo-R at the unique BamHI site of pAc510, a late transfer vector described previously by M. D. Summers and G. E. Smith, *A Manual of Methods for Baculovirus Vectors and Insect Cell Culture Procedures*. Texas Agricultural Experiment Station Bulletin No. 1555, Texas A&M University, (1987).

The plasmid pIE1FB was constructed by adding a BqlII BglII fragment from pDP500 (D. Panicali, A. Grzelecki and C. Huang, Gene, 47:193-199 (1986)), which encodes a functional *E. coli* β-galactosidase, at that site. This positions the β-galactosidase gene in frame at a site 36 base pairs downstream of the translational start site for IE1, fusing the first 12 amino acids of IE1 with the β-galactosidase fragment.

The plasmid pIE1NFB was constructed in similar fashion to the pIE1FB construct, except the BqlII fragment encoding β-galactosidase was inserted 39 base pairs upstream of the IE1 translational start site, at HincII, so that this plasmid encodes a nonfused β-galactosidase gene product.

The plasmid p39E+FB was analogous in construction to p39³⁰E Neo, except it contains the β-galactosidase coding sequence in place of the Neo-R coding sequence.

The plasmid pIE1tPA was analogous in construction to pIE1FB, except the BamHI fragment encoding tissue plasminogen activator (tPA) was inserted 39 base pairs upstream of the IE1 translational start site, at the HincII site, so that this plasmid encodes a nonfused tPA gene product.

Additionally, those skilled in the art who have the benefit of this disclosure will recognize that other plasmids can be prepared utilizing other heterologous genes of interest and other baculovirus early promoters.

EXAMPLE II

Construction of Stably-Transformed Insect Cell Clones

To construct a stably-transformed insect cell clone according to the present invention, a clonal derivative of the Lepidopteran insect cell line, designated Sf9, is used to generate stable genetic variants containing one or more of the novel genetic constructions described above. Sf9 cells were seeded at a density of about $1 \times 10^6$ in 35mm culture dishes and allowed to attach for at least one hour. The medium was removed, then the cells were cotransfected with a mixture of 2 μg of the plasmid containing heterologous DNA coding for a desired protein (e.g β-galactosidase) and 1 μg of pIE1Neo DNA, using established methods set forth in M. D. Summers and G. E. Smith, *A Manual of Methods for Baculovirus Vectors and Insect Cell Culture Procedures*, Texas Agricultural Experiment Station Bulletin No. 1555, Texas A&M University, (1987).

After transfection, the cells were incubated for 2 hours at 28° C., washed, and fed with TNMFH medium (M. D. Summers and G. E. Smith, (1987), supra: W. F. Hink, *Nature (London)*. 226:466-467 (1970)) supplemented with 10% fetal calf serum (Hazelton Research Products, Inc., Lenexa, Kans.) and antibiotics (complete TNMFH). The cells were incubated for another 22 hours at 28° C., then each dish was subcultured at low cell density to generate multiple sparsely-seeded 60 mm culture dishes. Each 60mm culture dish was typically seeded with approximately $5 \times 10^4$ cells. These were incubated for another 24 hours at 28° C., then the medium in each dish was replaced with fresh complete TNMFH containing 1 mg of the neomycin antibiotic, G418, (GIBCO; Grand Island, New York) per ml. The cultures were incubated at 28° C. for 1 week, the medium was replaced, and the cultures were incubated at 28° C. for another week. The medium then was replaced with complete TNMFH lacking G418 and the cultures were incubated at 28° C. until colonies were clearly visible to the naked eye. At that time, individual colonies were picked, and each was amplified until large enough numbers of cells were available for analysis. Once amplified, clones of interest were routinely grown at 28° C. in complete TNMFH, either as adherent or as suspension cultures.

EXAMPLE III

Evaluation of Promoters for Use in Continuous Expression of Heterologous Genes AcMNPV immediate-early and delayed-early promoters are exemplified by the IE1 and 39K promoters, respectively. However, those skilled in the art who have the benefit of this disclosure will recognize that other baculovirus early promoters may be utilized to advantage. The ability of these viral promoters to drive the constitutive expression of the antibiotic resistance Neo-R gene in stably-transformed Sf9 cells was established.

Sf9 cell cultures were transfected with different plasmids as constructed according to Example I (i.e., pIE1Neo, p39E−Neo, p39E+Neo, pIE139Neo, p510Neo, pIE1FB, pIE1NFB, p39E+FB, pIE1tPA), washed, and incubated for 24 hours at 28° C. These cell cultures were then subcultured to produce 24 plates (60 mm diameter) seeded with equal numbers of cells. Twelve of the plates from each culture were seeded with cells in fresh TNMFH, while the other 12 were seeded in fresh TNMFH containing 1 mg of the antibiotic G418 per ml. To establish the number of cells initially seeded into each dish, viable cell counts were performed on triplicate samples of the starting cell suspensions, using the standard trypan blue exclusion staining techniques as described in M. D. Summers and G. E. Smith, *A Manual of Methods for Baculovirus Vectors and Insect Cell Culture Procedures*, Texas Agricultural Experiment Station Bulletin No. 1555, Texas A&M University (1987). Subsequently, triplicate plates were counted either at 2- or 4-day intervals, for either control- or G418-treated cells, respectively.

Regardless of the plasmid used for transfection, all of the cells had approximately equivalent growth curves in the absence of the antribiotic G418. Moreover, these growth curves were typical of normal, untransfected Sf9 cells. This indicated that none of the plasmids had a severely toxic effect over the time period studied. In the presence of the antibiotic G418, cells that were transfected with p510Neo did not survive. This result was consistent with the idea that expression of the Neo-R gene from the very late polyhedrin promoter requires the previous expression of a number of other viral genes (L. K. Miller, *Annual Review of Microbiol.*, 42:177–199 (1988)) which were absent in these cells. In contrast, large numbers of G418-resistant cells were obtained when Sf9 cells were transfected with pIE1Neo or p39E+Neo plus pIE1. These results show that either the IE1 promoter or the 39K promoter can be used to continuously express the Neo-R gene product in Sf9 cells. It should be noted that these promoters, and other baculovirus early promoters could drive the continuous expression of other heterologous gene products, as well, such as, β-galactosidase, tissue plasminogen activator, human interleukin-2, and human β-interferon, for example. It should also be noted that other antibiotic-resistance genes, such as those encoding resistance to hygromycin B or methotrexate could be used to advantage in addition to those encoding resistance to neomycin.

The results also established the influence of the IE1 gene product and the exemplary transcriptional enhancer element, hr5 (L. A. Guarino and M. D. Summers, *J. Virol.*, 60:215–223 (1986b); L. A. Guarino, M. A. Gonzalez and M. D. Summers, *J. Virol.*, 60:224–229 (1986)), on continuous gene expression from the 39K promoter. The smallest numbers of G418-resistant cells were obtained by transfection with p39E−Neo in the absence of IE1. Transfection with p39E−Neo in the presence of IE1 or with p39E+Neo in the absence of IE1 produced larger numbers of G418-resistant cells. The largest numbers were obtained in the presence of both IE1 and hr5. These results are in agreement with the results of previous transient expression assays, which have established that expression from the 39K promoter is activated in trans by the IE1 gene product and in cis by hr5 (L. A. Guarino and M. D. Summers, *J. Virol.*, 57:563–571 (1986a); *J. Virol.*. 60:215–223 (1986b)). Interestingly, approximately equivalent numbers of resistant cells were obtained by using either the IE1 promoter alone or the 39K promoter in the presence of both IE1 and hr5. Based upon these observations, either the IE1 promoter alone or the 39K promoter in the presence of IE1 and the AcMNPV transcriptional enhancer element hr5 are equally effective as promoters for the production of stably-transformed Sf9 cell variants capable of continuous foreign gene expression. It should also be noted that in addition to hr5, the AcMNPV transcriptional enhancer elements hr1, hr2, hr3 and hr4 could be utilized to advantage.

EXAMPLE IV

Construction of Stably-transformed Sf9 Cells Expressing E. coli β-galactosidase from Baculovirus Early Gene Promoters To generate stably-transformed variants that continuously express *E. coli* β-galactosidase, Sf9 cells were cotransfected with the plasmids of Example I as follows: pIE1FB plus pIE1Neo, pIE1NFB plus pIE1Neo, or p39E+FB plus pIE1 and pIE1Neo. After cotransfection, G418-resistant cells were selected, and colonies were isolated as described in Examples I–III. Well-isolated colonies were picked and amplified. Cytoplasmic extracts were then prepared from the individual clones and assayed for β-galactosidase activity (Table 1). β-galactosidase activity was detected in over one-half of the clones isolated after transfection with IE1FB or IE1NFB and in more than one-third of those isolated after transfection with p39E FB. The clone designated IE1FB2 had the highest activity, which was about 5–15% of that transiently expressed in Sf9 cells infected for 24 hours with Ac360-βgal or VL720-βgal. Ac360-βgal and VL720-βgal are recombinant baculoviruses in which transient expression of the β-galactosidase gene is driven by the polyhedrin promoter (See M. D. Summers and G. E. Smith, *A Manual of Methods for Baculovirus Vectors and Insect Cell Culture Procedures*, Texas Agricultural Experiment Station Bulletin No. 1555, Texas A&M University (1987), regarding Ac360-βgal and V. A. Luckow and M. D. Summers, *Virol.*, 167:56–71 (1988b), regarding VL720-βgal). Further analysis showed that three of the four positive IE1FB clones expressed β-galactosidase continuously for at least 29 passages in culture (Table 2). The clone IE1FB2 expressed β-galactosidase activity continuously for over 55 passages, as shown in Table 2. The IE1FB5 clone, which lost the ability to express β-galactosidase, lacked integrated plasmid DNA sequences after about 20 passages. These results indicated that the IE1FB cells, in general, expressed less β-galactosidase after about 55 passages than after 3-4 passages. However, the level of expression stabilized by passage number 30, evidencing that continuous expression of a foreign gene was achieved in a stably-transformed cell line.

TABLE 1

β-gal activity in extracts of stably-transformed Sf9 clones.

| Clone | β-Gal U/10⁶ Cells | Clone | β-Gal U/10⁶ Cells | Clone | β-Gal U/10⁶ Cells |
|---|---|---|---|---|---|
| IE1FB1 p4 | 0.000 | IE1NFB1 p3 | 0.000 | 39E + FB1 p1 | 0.000 |
| IE1FB2 p4 | 0.479 | IE1NFB2 p2 | 0.012 | 39E + FB2 p1 | 0.000 |
| IE1FB4 p4 | 0.021 | IE1NFB3 p3 | 0.002 | 39E + FB3 p1 | 0.015 |
| IE1FB5 p4 | 0.079 | IE1NFB4 p2 | 0.011 | 39E + FB4 p1 | 0.001 |
| IE1FB6 p3 | 0.001 | IE1NFB5 p1 | 0.030 | 39E + FB5 p1 | 0.000 |
| IE1FB7 p3 | 0.025 | IE1NFB6 p2 | 0.002 | 39E + FB6 p1 | 0.000 |
| IE1FB8 p3 | 0.000 | IE1NFB7 p1 | 0.011 | 39E + FB7 p1 | 0.000 |
|  |  | IE1NFB8 p1 | 0.054 | 39E + FB8 p1 | 0.005 |
|  |  | IE1NFB9 p1 | 0.022 | 39E + FB9 p4 | 0.003 |
| Sf9 | 0.000 | IE1NFB10 p3 | 0.030 | 39E + FB14 p3 | 0.003 |
| Sf9/720βGal |  | IE1NFB11 p3 | 0.158 | 39E + FB16 p3 | 0.001 |
| Undiluted | 4.390 | IE1NFB12 p3 | 0.018 | 39E + FB17 p3 | 0.001 |
| 1:10 | 0.920 |  |  | 39E + FB18 p2 | 0.004 |
| 1:100 | 0.275 |  |  | 39E + FB20 p2 | 0.000 |
| Sf9/360βGal |  |  |  | 39E + FB21 p2 | 0.011 |
| Undiluted | 3.585 |  |  | 39E + FB22 p3 | 0.000 |
| 1:10 | 0.372 |  |  |  |  |
| 1:100 | 0.008 |  |  |  |  |

TABLE 2

Effect of passage on β-gal activity.

| Clone/Passage | β-Gal U/10⁶ Cells |
|---|---|
| IE1FB1 p4 | 0.000 |
| IE1FB1 p31 | 0.000 |
| IE1FB2 p4 | 0.479 |
| IE1FB2 p23 | 0.092 |
| IE1FB2 p31 | 0.134 |
| IE1FB2 p55 | 0.128 |
| IE1FB4 p4 | 0.021 |
| IE1FB4 p30 | 0.016 |
| IE1FB5 p4 | 0.079 |
| IE1FB5 p29 | 0.000 |
| IE1FB7 p3 | 0.025 |
| IE1FB7 p29 | 0.004 |

To verify the presence of β-galactosidase-related polypeptides in the transformed Sf9 cell clones, the cells were pulse-labeled, detergent-extracted, and the immunoprecipitates were analyzed by SDS-PAGE. The pIE1FB-transformed clones 2, 4 and 7 described here each contained a specifically immunoreactive polypeptide with an apparent molecular weight of about 120,000. This polypeptide was not detected in mock- or AcMNPV-infected Sf9 cells or in the IE1FB-transformed clones 1 or 5 (note that clone 5 was initially positive, but reverted with passage; Table 2). This polypeptide comigrated with a similar recombinant product expressed by Ac360-βgal, in which the first 11 amino acids of polyhedrin were fused in frame to β-galactosidase (M. D. Summers and G. E. Smith, *A Manual of Methods for Baculovirus Vectors and Insect Cell Culture Procedures*, Texas Agricultural Experiment Station Bulletin No. 1555, Texas A&M University (1987)). Thus, by the criteria of specific immunoreactivity, molecular size, and enzymatic activity, the polypeptide produced by the procedures described herein represented the authentic IE1-βgalactosidase fusion product.

A comparison of the relative mounts of the β-gal synthesized by the different Sf9 cell transformants in a 4-hour labeling period revealed that the IE1FB2 clone produced the largest amount of β-gal. On the average, the IE1 fusion constructs (IE1FB) expressed larger amounts of β-gal than the nonfused IE1 (IE1NFB) constructs, and the 39K constructs (39FB) expressed less than the IE1 constructs. Significantly higher amounts of β-gal were labeled in Sf9 cells infected with Ac360-βgal in a transient BEV system than in any of the stably-transformed cells. This reflects a much higher rate of β-gal synthesis in the infected cells during the four hour labeling period. Curiously, IE1FB2 cells at a higher passage level (P41) actually produced more radiolabeled β-gal during the four hour labeling period than the same cells at a lower passage level (P8).

Immunofluorescence microscopy was performed to examine the intracellular distribution of β-galactosidase in the IE1FB2 cells. Normal Sf9 cells were not stained, while VL720-β-gal infected Sf9 cells exhibited intense cytoplasmic fluorescence. Although the reaction is much less intense, a similar distribution of fluorescence was observed in IE1FB2 cells. Phase microscopy revealed that the overall morphology of IE1FB2 cells is quite similar to that of Sf9 cells.

Western blotting analysis was performed to examine the total amounts of β-gal that accumulated in each clone in 24, 48, or 72 hours of growth. The results verified that there was significantly less β-gal in the stably-transformed cells than in the transient BEV infected cells at corresponding times post-infection (note that tenfold less of the infected cell extracts was loaded in each case). The amounts of β-gal produced by IE1FB2 at various passage levels were compared to serial dilutions of an extract from the transient BEV 360-βgal-infected cells. The amount of β-galactosidase produced in the IE1FB2 clone was higher than that produced in Sf9 cells transfected amount produced between 20-24 hours post infection in Sf9 cells infected with the Ac360-βgal transient BEV system. The relative amounts of β-galactosidase labeled during the 4 hour pulse of each cell type was determined by excising the β-galactosidase bands, solubilizing the gel slices, and counting the radioactivity. After 48 hours of growth, IE1FB2 contained about 0.1–0.5% of the total β-gal-related protein in Sf9 cells infected for 48 hours with 360-β-gal in a transient BEV system. Similar amounts of β-gal were detected in IE1FB2 at different passage levels, ranging from P23 to P55. Finally, both immunoprecipitation and western blotting revealed that the transient BEV infected cell extracts contained large amounts of numerous β-gal-related polypeptides smaller than the intact β-gal product. Thus, while the transient BEV infected cells produce significantly larger amounts of β-gal than the stably-transformed cells of this invention, the product from the transient BEV system is contaminated with relatively larger amounts of what are probably degradation products, even at relatively early times (24 hours) post-infection.

Genetic Analysis

Genetic analysis of β-gal expression in Sf9 cells transformed with IE1-β-gal constructs was performed to verify that the heterologous DNA sequence encoding for the foreign gene (here β-galactosidase) was stably integrated into the host cell chromosome. Total cellular DNA was extracted from Sf9 cells or from various IE1FB clones and digested with EcoRI. The digests were resolved by gel electrophoresis, transferred to nitrocellulose filters, and the filters were hybridized with radiolabeled pIE1FB probes as described in Examples I-III. Plasmid-specific sequences were detected in the DNA isolated from IE1FB clones 2, 4, and 7, but not from Sf9 cells or IE1FB clones 1 or 5. These pIE1FB-specific sequences were present in significantly higher copy number in the DNA from IE1FB2 as compared to IE1FB clones 4 and 7; these contained approximately equivalent amounts of plasmid specific DNA, but much less than IE1FB2. Thus, the relative amounts of plasmid-specific DNA corresponded to the relative levels of β-galactosidase activity expressed by these clones. The results obtained also suggest that the loss of β-gal activity in IE1FB5 (positive at P4 but negative at P29; Table 2) resulted from loss of the pIE1FB-related sequences at some point prior to P19. In contrast, IE1FB2 DNA still contained significant amounts of pIE1FB-related sequences at P55, indicating that these sequences are maintained stably in this clone. The Southern blots of total cellular DNA suggest that pIE1FB is integrated in IE1FB clones 2, 4 and 7. The plasmid-specific DNA in IE1FB7 occurs primarily as offsize restriction fragments. Moreover, offsize restriction fragments also are detectable in IE1FB2 and IE1FB4 DNA in longer exposures of the autoradiograms. However, the hybridization patterns of the latter two clones suggest that they contain tandem repeats of the integrated plasmid DNA. Finally, the multiple offsize restriction fragments detected in DNA from IE1FB2 suggests that the plasmid may be integrated at several sites in this clone.

S1 nuclease protection assays were performed to determine if the pIE1FB-related sequences integrated in the IE1FB clones were transcribed. Total cellular RNA was extracted from the cells at passage 18 and S1 mapping was carried out with 5' end-labeled pIE1Neo and pIE1FB fragments as probes. A 168 base pair fragment of the pIE1Neo probe was protected by RNA from each of the IE1FB clones, but not by RNA from untransformed Sf9 cells. This shows that the antibiotic resistance Neo-R gene is transcribed in each of the IE1FB clones, a result which is corroborated by their ability to survive in the presence of the antibiotic G418. It also shows that transcription initiates specifically within the IE1 promoter. A 293 base pair fragment of the pIE1FB probe was protected by RNA from IE1FB2 and IE1FB4, but not by RNA from untransformed Sf9 cells or from IE1FB1, IE1FB5, or IE1FB7. Again, this shows that the integrated sequences are transcribed and that transcription initiates specifically within the IE1 promoter. Moreover, the relative amounts of RNA expressed in the different IE1FB clones, revealed by the degree of nuclease protection, corresponded closely with the amounts of β-gal fusion protein produced. This suggests that the differences observed in the relative amounts of β-gal produced by the various IE1FB clones depend upon differences in the total levels of transcription of the integrated plasmid DNA sequences.

EXAMPLE V

Construction of Stably-Transformed Sf9 Cells Continuously Expressing Human Tissue Plasminogen Activator from the IE1 Promoter Using the methods detailed in Examples I-IV, stably-transformed variants were constructed which continuously express human tissue plasminogen activator (tPA). In similar fashion to Example IV, Sf9 cells were cotransfected with pIE1tPA plus pIE1Neo. After transfection, G418-resistant cells were selected, and colonies were isolated as described in Examples I-III. Well-isolated colonies were picked and amplified. Similar to Example IV, to verify the presence of tPA related polypeptides in the transformed Sf9 cell clones, the cells were pulse-labeled, detergent-extracted, and immunoprecipitates were analyzed by SDS-PAGE. Several of the clones expressed a polypeptide which, by the criteria of immunoreactivity and molecular size was identical to authentic tPA. The pIE1tPA-transformed clones expressed significantly less activity than that expressed in Sf9 cells infected for 24 hours with 941-tPA. 941-tPA is a recombinant baculovirus in which expression of the tPA gene is driven by the polyhedrin promoter in a transient BEV system. (See D. L. Jarvis and M. D. Summers, *Mol. Cell. Biol.*, 9:214–223 (1989)).

Although the amount of tPA expressed by the stably-transformed cell line was less than the amount expressed by the BEV system, the amount of tPA secreted was virtually identical in both systems. Significantly, almost all of the tPA expressed in the stably-transformed cell lines was secreted, indicating that the ability of the transformed cell to process newly synthesized proteins remained unaltered. In direct contrast, only a small fraction of the tPA expressed by the BEV system was secreted due to the late viral effects adversely impacting the cell's ability to process the foreign gene product.

Further modifications of the invention herein disclosed will occur to persons skilled in the art who have the benefit of this disclosure, and all such modifications are deemed to be within the spirit and scope of the invention as defined by the appended claims.

What is claimed is:

1. A stably-transformed Lepidopteran insect cell line for constitutive heterologous gene expression comprising a DNA coding for a selectable marker gene and heterologous DNA coding for a desired protein operably linked down stream of baculovirus EII immediate early gene promoter region which is stably incorporated into the genome of said insect cell line.

2. The stably-transformed Lepidoptera cell line of claim 1 wherein said Lepidoptera cell line is *Spodoptera frugiperda* or *Trichoplusia ni*.

3. The stably-transformed insect cell line of claim 1 wherein said homologous DNA is the gene encoding tissue plasminogen activator.

4. The stably-transformed insect cell line of claim 1 wherein said heterologous DNA is the gene encoding β-galactosidase.

5. The stably-transformed Lepidoptera cell line of claim 1 wherein said baculovirus IE1 immediate early gene promoter region is derived from the viral DNAs of *Autographs californica* MNPV, *Tricoplusia ni MNPV*, *Rachiplusia ou* MNPV or *Galleria mellonella* MNPV.

6. The stably-transformed Lepidoptera cell line of claim 1 further comprising DNA coding for baculovirus 39K delayed-early gene promoter and an enhancer, selected from the group consisting of hr1, hr2, hr3, hr4 and hr5.

* * * * *

UNITED STATES PATENT AND TRADEMARK OFFICE
CERTIFICATE OF CORRECTION

PATENT NO. : 5,077,214

DATED : December 31, 1991

Page 1 of 2

INVENTOR(S) : Linda A. Guarino; Donald L. Jarvis

It is certified that error appears in the above-identified patent and that said Letters Patent is hereby corrected as shown below:

Column 16,

Claim 1, line 5, "EIl" should be --IEl--;

Claim 3, line 2, "homologous" should be --heterologous--;

In the Abstract, line 6, "30K" should be --39K--.

Column 1, lines 20 and 34, "*Too.*" should be --*Top.*--; line 58, "J. Virol.," should be --*J. Virol.*,--; and line 62, "gene" should be --genes--.

Column 4, line 55, "membrane-bound-glycopro-" should be --membrane-bound glycopro--.

Column 5, line 51, "Colelction" should be --Collection--.

Column 6, line 34, "8-galactosidase" should be --ß-galactosidase--; and line 47, "isolatd" should be --isolated--.

Column 7, line 41 "pAc360-8-gal," should be --pAc360-ß-gal,--.

Column 9, line 8, "25 Berg," should be --Berg,--; line 15, "p39E+Neo" should be --p39E$^+$Neo--; line 19, "6):215-223" should be --60:215-223--; lines 27, 48, and 66 "BqlII" should be --BglII--; line 44, "p39E$^+$Neo" should be --p39E$^+$Neo.--; line 50, "BqlII-BamHI" should be --BglII-BamHI--; line 58, "BqlII" should be --BglII linker at the Eco47III site of pAcIEl, then inserting a--; and line 59, "Gene" should be --*Gene*--.

Column 10, line 4, "p39$^{30}$E Neo," should be --p39E$^+$Neo,--; and "8-galactosi-" should be --ß-galactosi--; and line 34, "(e.g" should be --(e.g.--.

Column 12, line 3, "p39E Neo" should be --p39E$^+$Neo--; and line 44, "p39E FB." should be --p39E$^+$FB.--

Column 13, line 61, "mounts" should be --amounts--.

UNITED STATES PATENT AND TRADEMARK OFFICE
CERTIFICATE OF CORRECTION

PATENT NO. : 5,077,214

DATED : December 31, 1991

INVENTOR(S) : Linda A. Guarino; Donald L. Jarvis

It is certified that error appears in the above-identified patent and that said Letters Patent is hereby corrected as shown below:

Column 14, line 48, "360-ßgal-" should be --360-ßgal---; and line 51, after "transfected", insert --with pIElFB DNA, but it was significantly lower than the--.
Column 16, line 45, "gene" should be --gene,--.

Signed and Sealed this

Sixteenth Day of November, 1993

Attest:

BRUCE LEHMAN

Attesting Officer

Commissioner of Patents and Trademarks